United States Patent
Prezewowsky et al.

[11] 3,951,958
[45] Apr. 20, 1976

[54] 1,3-OXYGENATED-8α-ESTRATRIENES

[75] Inventors: Klaus Prezewowsky; Henry Laurent; Helmut Hofmeister; Rudolf Wiechert; Friedmund Neumann; Yukishige Nishino, all of Berlin, Germany

[73] Assignee: Schering Aktiengesellschaft, Berlin and Bergkamen, Germany

[22] Filed: July 12, 1974

[21] Appl. No.: 487,988

[30] Foreign Application Priority Data
July 13, 1973 Germany............................ 2336434
July 13, 1973 Germany............................ 2336433
May 31, 1974 Germany............................ 2426778
May 31, 1974 Germany............................ 2426779

[52] U.S. Cl. .................. 260/239.5; 260/239.55 R; 260/239.55 D; 260/397.4; 260/397.5
[51] Int. Cl.² ........................................ C07J 71/00
[58] Field of Search...... 260/397.4, 397.5, 239.55 D

[56] References Cited
UNITED STATES PATENTS
3,686,238   8/1962   Zaffaroni............................ 260/399

*Primary Examiner*—Elbert L. Roberts
*Attorney, Agent, or Firm*—Millen, Raptes & White

[57] ABSTRACT
1,3-Dihydroxy-8α-estratrienes of the formula

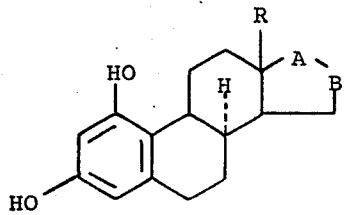

wherein R is lower-alkyl and —A—B is

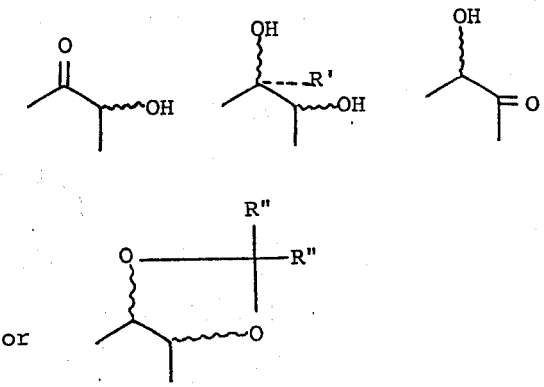

or wherein R' is a saturated or unsaturated hydrocarbon group and R" is lower-alkyl, aralkyl or phenyl, and the esters and ethers thereof, possess strong vaginotropic but only weak utertropic activity and are useful in the treatment of estrogenic deficiency conditions where uteral effects are not desired.

42 Claims, No Drawings

1,3-OXYGENATED-8α-ESTRATRIENES

BACKGROUND OF THE INVENTION

This invention relates to novel 1,3-oxygenated-8α-estratrienes.

SUMMARY OF THE INVENTION

In a composition aspect this invention relates to 1,3-oxygenated-8α-estratrienes of the general Formula I

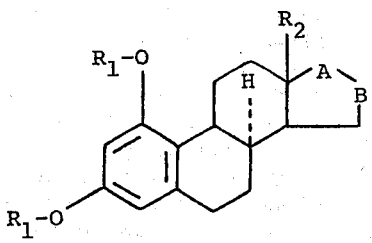

wherein —A—B— is

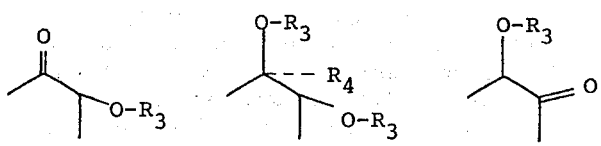 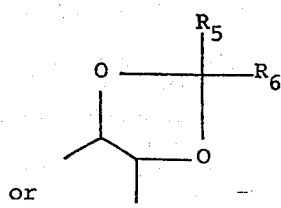

or and the —O—R₃-groups can be in the α- or β-position and the alkylenedioxy groups can be in the 16α, 17α- or 16β, 17β-position, wherein $R_1$, $R_3$ each are a hydrogen atom, acyl, alkyl, cycloalkyl or an oxygen-containing saturated heterocyclic group; $R_2$ is lower alkyl; $R_4$ is a hydrogen atom or a substituted or unsubstituted, saturated or unsaturated hydrocarbon group, and $R_5$ and $R_6$, which can be alike or different, each are a hydrogen atom, lower alkyl, aralkyl, or an optionally substituted phenyl group.

In another composition aspect, this invention relates to pharmaceutical compositions comprising a vaginotropic effective amount of a compound of this invention in admixture with a pharmaceutically effective carrier.

DETAILED DISCUSSION

Suitable acyl groups are those of any physiologically acceptable acid, including sulfonic and carboxylic acids. Preferred acyl groups are those of hydrocarbonic carboxylic acids and sulfonic acids of 1–15 carbon atoms, including those of the aliphatic, cycloaliphatic, aromatic, aromatic-aliphatic series. Equivalent of these are those of the heterocyclic series and those which are unsaturated and/or polybasic and/or substituted in the usual manner, e.g., by alkyl, hydroxy, alkoxy, oxo, or amino groups, or halogen atoms.

Examples of suitable carboxylic acids are alkanoic acids of 1–15, preferably 2–8 carbon atoms, e.g., formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert.-butylacetic acid, and cycloalkylalkanoic acids wherein cycloalkyl and alkanoic are as defined herein, e.g., cyclopentylacetic acid, cyclohexylacetic acid, cyclohexanecarboxylic acid and aryl carbocyclic carboxylic acid and aryl carbocyclicalkanoic acids of 7–15, preferably 7–12, carbon atoms, e.g., benzoic and phenylacetic acid. Equivalents of these acids are, e.g., phenoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, nicotinic acid, isonicotinic acid, furan-2-carboxylic acid.

Examples of sulfonic acids are alkanesulfonic acids of 1–6 carbon atoms, e.g., methanesulfonic acid, ethanesulfonic acid, butanesulfonic acid, cycloalkanesulfonic acids of 3–8 carbon atoms, e.g., cyclopentanesulfonic acid and cyclohexanesulfonic acid, and aryl carbocyclicsulfonic acids of 6–12 carbon atoms, e.g., benzenesulfonic acid and p-toluenesulfonic acid. Examples of equivalents of these acids are β-chloroethanesulfonic acid, p-chlorobenzenesulfonic acid, N,N-dimethylaminosulfonic acid, N,N-diethylaminosulfonic acid, N,N-bis (β-chloroethyl) aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acid.

Preferred $R_1$ or $R_3$ alkyl groups are lower alkyl of 1–5 carbon atoms, which can be branched in the usual manner. Especially preferred are methyl and ethyl. Equivalents are those substituted in the usual manner, e.g., by a halogen atom, preferably chlorine, or lower alkoxy, preferably methoxy.

Examples of cycloalkyl groups are those of 3–8 carbon atoms, e.g., cyclopentyl, cyclopropyl, cyclohexyl, cycloheptyl and the corresponding rings bearing, e.g., 1–3 alkyl, preferably methyl, groups. Cyclopentyl group is preferred.

An example of a saturated oxygen-containing heterocyclic group is tetrahydropyranyl, which is preferred. Equivalent are any other such groups derived from heterocycles of at least one oxygen atom in the ring and which are perhydrogenated in the oxygen-containing ring, e.g., tetrahydrofuryl.

Examples of hydrocarbon $R_4$ groups are saturated and mono-unsaturated hydrocarbon of up to 6 carbon atoms, viz., alkyl, alkenyl and alkinyl, e.g., methyl, ethyl, propyl, butyl, pentyl, hexyl, vinyl, ethinyl and propenyl. Equivalents are di-unsubstituted groups, e.g., butadienyl, butadiynyl and corresponding hydrocabon groups bearing the usual substituents, e.g., halogen, preferably chloro. Preferred hydrocarbon and substituted hydrocarbon groups are ethinyl and chloroethinyl, respectively.

Examples of $R_2$ are lower alkyl groups of 1–4 carbon atoms, e.g., methyl, ethyl, propyl and butyl, preferably methyl or ethyl.

Examples of $R_5$ and $R_6$ are alkyl of 1–5 carbon atoms, e.g., methyl, ethyl, propyl and butyl, preferably methyl or ethyl. Examples of preferred aralkyl groups are those of 7–10 carbon atoms, wherein aryl is monocyclic carbocyclic and aryl is lower-alkyl, e.g., phenylbutyl, phenylethyl and benzyl, of which benzyl is preferred. Equivalents are those wherein the phenyl group bears a substituent, e.g., one or more halogen atoms and lower alkyl groups, as well as hydroxyl, alkoxy, nitro and amino groups.

Preferred compounds of Formula I are those wherein a. —A—B— is 16-O-$_3$, 17-one wherein $R_2$ is methyl or ethyl and $R_1$ and $R_3$ are alike or different and are hydrogen atoms, alkyl of 1–4 carbon atoms, preferably methyl, or alkanoyl of 2–8 carbon atoms, preferably acetyl;

b. —A—B— is 16-O-$R_3$, 17α-$R_4$, 17β-O-$R_3$ wherein $R_2$ is methyl or ethyl and $R_1$ and $R_3$ are alike or different and are hydrogen atoms, alkyl of 1–4 carbon atoms, preferably methyl, or alkanoyl of 2–8 carbon atoms, preferably acetyl; and $R_4$ is a hydrogen atom or when $R_3$ is a hydrogen atom, ethinyl;

c. —A—B— is 16-keto-17β-O-$R_3$ wherein $R_2$ is methyl or ethyl and $R_1$ and $R_3$ are alike or different and are hydrogen atoms, alkyl of 1–4 carbon atoms, preferably methyl, or alkanoyl of 2–8 carbon atoms, preferably acetyl;

d. —A—B— is an alkylidenedioxy group wherein $R_5$ and $R_6$ each are lower-alkyl, preferably methyl, $R_2$ is methyl or ethyl and $R_1$ and $R_3$ are alike or different and are hydrogen atoms, alkyl of 1–4 carbon atoms, preferably methyl, or alkanoyl of 2–8 carbon atoms, preferably acetyl;

e. those of (a)–(d) wherein both $R_1$ are alike and are hydrogen atoms, alkyl of 1–4 carbon atoms, preferably methyl, or alkanoyl of 2–8 carbon atoms, preferably acetyl, the 16-position substituent is —O-$R_3$, preferably α-O-$R_3$, wherein $R_3$ is as defined herein and the 17-position substituent is keto or α-ethinyl-β-ol;

f. those of (a)–(d) wherein $R_2$ is methyl or ethyl, both $R_1$ groups are alike and each are hydrogen atoms, methyl or acetyl, $R_3$ is $R_1$ as defined herein, $R_4$ is a hydrogen atom or, when O$R_3$ is hydroxy, ethinyl.

The compounds of this invention have an advantageous dissociated pharmacological activity, viz., strongly vaginotropic and weakly uterotropic effectiveness, they are preferably suitable for the treatment of estrogen deficiency where an estrogenic effect on the vaginal epithelium is desired, but an estrogenic effect on the uterus is to be avoided if possible. For example, they are suitable for the treatment of females in the postmenopausal period.

The compounds of this invention are also useful as intermediates for the preparation of other pharmacologically useful steroids.

The favorable estrogenic dissociation can be shown, for example, in the sialic acid test on mice. The sialic test is conducted as follows:

The mice are ovariectomized. Starting with the 10th day after castration, the animals receive the substance to be tested once daily for 3 days. On the fourth day, the animals are sacrificed. Vagina and uterus are immediately excised and weighted into a test tube for hydrolysis. The determination of the sialic acid is conducted according to Svennerholm [Biochem. Biophys. Acta 24 (1957) 604]. The increase in the organ weights of vagina and uterus in dependence on the dose, as well as the reduction in the sialic acid content are determined, deriving therefrom the relative effective strength of the compound to be tested compared to the standard, estradiol (II). The relative effectivenesses are converted into a ratio and result in the degree of dissociation, Q. For the standard compound estradiol, Q = 1. Compounds with Q > 1 are primarily vaginotropic, and with Q < 1 are primarily uterotropic.

The threshold values indicated in Table 1 were determined on rats in the usual Allen-Doisy test.

In this test, the compounds of this invention exhibit a dissociation quotient far surpassing that of the standard compounds, as shown in Table 1, in which the standard estrogens, 17α-ethinyl-1,3,5-(10)-estratriene-3,17α-diol (I) and 1,3,5-(10)-estratriene-3,17β-diol (II), are compared with the compounds of this invention, 1,3,16α-triacetoxy-8α-estra-1,3,5(10)-trien-17-one (III), 1,3-diacetoxy-16β, 17β-isopropylidenedioxy-8α-estra-1,3,5(10)-triene (IV), and 1,3,16α-triacetoxy-17α-ethinyl-8α-estra-1,3,5(10)-trien-17β-ol (V).

TABLE 1

| No. | Name | Threshold Value [mg] | | Dissociation Quotient | |
|---|---|---|---|---|---|
| | | s.c. | p.o. | s.c. | p.o. |
| I | 17α-Ethinyl-1,3,5-(10)-estratriene-3,17β-diol | 0.0003 | 0.01 | 0.4 | 0.8 |
| II | 1,3,5(10)-Estratriene-3,17β-diol | 0.0005 | 0.05–0.1 | 1.0 | 1.0 |
| III | 1,3,16α-Triacetoxy-8α-estra-1,3,5(10)-trien-17-one | | | 4.0 | |
| IV | 1,3-Diacetoxy-16β,-17β-isopropylidenedioxy-8α-estra-1,3,5(10)-triene | 0.3 | | | 2.1 |
| V | 1,3,16α-Triacetoxy-17α-ethinyl-8α-estra-1,3,5(10)-trien-17β-ol | 0.01 | | 1.9 | |

This invention also relates to pharmaceutical composition comprising an 8α-estratriene of general Formula I in admixture with a pharmaceutical carrier.

Such compositions are produced in the usual manner by formulating the effective agents into the desired forms of application, e.g., tablets, dragees, capsules, oral and injectable solutions, employing the usual vehicles, diluents, flavorameliorating agents, etc. customary in galenic pharmacy.

The effective agent concentrations in the thusformulated drugs is dependent on the mode of administration. Thus, a tablet preferably contains 0.01–10 mg.; solutions for parenteral administration preferably contain 0.1–20 mg./ml. of solution.

As will be apparent to those skilled in the art, the dosage of the medicinal agents of this invention can vary with the type of administration and the respectively selected compound. Moreover, the dosage can vary from patient to patient. In general, the compounds of the present invention are administered at a dosage level which can achieve the desired results without causing any disadvantageous or deleterious side effects. Thus, the compounds are administered, for example, at a dosage level ranging from approximately 0.02 mg. to about 20 mg., although modifications can be made under certain circumstances, so that a dosage level of more than 20 mg., for example up to 50 mg., is employed. However, a dosage level in the range of about 0.03 mg. to approximately 5 mg. is preferred.

The compounds of general Formula I can be prepared by oxidizing in a conventional manner an enol acylate of general Formula II

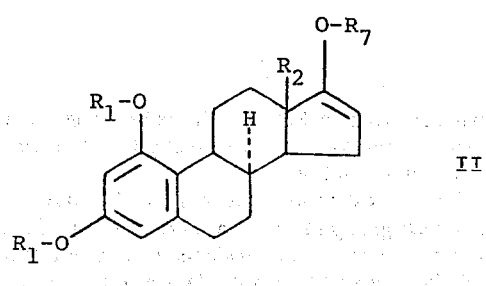

wherein $R_1$ and $R_2$ have the values given above, $R_7$ is acyl, e.g., as defined above for $R_1$ and $R_3$, and optionally thereafter isomerizing and/or reducing and/or splitting off ether or acyl groups and/or esterifying and/or etherifying free hydroxyl groups, depending on the desired final value for A–B.

In the oxidation of compounds of general Formula II, $R_7$ is an acyl group customarily employed for the protection of hydroxy groups during reactions which would otherwise undesirably alter the hydroxy group and preferably is the same as that desired in the final product, e.g., acetyl, butyryl and heptanoyl. The oxidation can be accomplished with peracids, e.g., perbenzoic acid, peracetic acid, m-chloroperbenzoic acid and monoperphthalic acid. The oxidation can, however, also be conducted with other mild oxidizing agents, for example a lead tetraacylate, e.g., lead tetraacetate.

Various processes are known to a person skilled in the art for conducting the optional measures to which the oxidation product can subsequently be subjected, e.g., those described hereinbelow.

If the product of the oxidation is a 17β-acyloxy-16α,17α-epoxy compound, the subsequent isomerization can be effected by reaction with an acid, e.g., sulfuric acid or perchloric acid, as well as by treatment with an isomerization catalyst, e.g., silica gel or an aluminosilicate, or by heating to above its melting point. If the oxidation product is a 17-keto-16β-acylate, the isomerization can be effected with a strong base, among which the alkalies are preferred, e.g., a potassium hydroxide solution, soda solution or a sodium hydroxide solution.

A 17-keto group present in the oxidation product can subsequently be reduced in accordance with known methods. Thus, the reduction can be accomplished by reaction with hydrogen in the presence of a conventional catalyst, e.g., Raney nickel, platinum. The hydrogen atom can also be transferred to the 17-keto group from a metal hydride. Especially suitable as the hydrogen donors are the complex hydrides, such as, for example, sodium hydridoborate, lithium hydridoaluminate, sodium hydridotrimethoxoborate and lithium hydridotri-tert.-butoxoaluminate.

The reduction can also be effected according to conventional methods with an organometallic compound whose organic group is the desired $R_4$ group, e.g., an alkylmagnesium halide, such as, for example, methylmagnesium bromide or iodide, an alkenylmagnesium and/or alkenylzinc halide, e.g., vinylmagnesium bromide or allylmagnesium bromide, an alkinylmagnesium halide, e.g., ethinylmagnesium bromide, propinylmagnesium bromide or propinylzinc bromide, or an alkali metal acetylide, e.g, potassium acetylide.

The organometallic compound utilized as the reducing agent can also be formed in situ and made to react with the 17-ketone. Thus, for the reaction with organometallic alkinyl, the ketone is treated, for example, in a suitable solvent with an alkine, chloroalkine or alkadiyne, and an alkali metal, preferably in the presence of a tertiary alcohol or ammonia, optionally under elevated pressure.

A 16-keto group can subsequently be reduced according to conventional methods, e.g., with a metal hydride or with hydrogen obtained in the nascent state from sodium and an alcohol.

An epoxy group contained in the oxidation product can be reduced. The reduction can be carried out, inter alia, by catalysis, e.g., with hydrogen in the presence of a metallic catalyst, e.g., platinum or palladium, or with a reducing agent, e.g., a hydrido compound, for example, $LiAlH_4$, or a dialkylaluminum hydride, e.g., diisobutylaluminum hydride.

Free hydroxy groups can subsequently be esterified or etherified. Esterified or etherified hydroxy groups can be converted into the hydroxy groups. These process steps are also conducted according to methods known per se.

The acylation in the 1- and 3-positions is preferably conducted with pyridine and the selected acid anhydride and/or with pyridine/acid chloride at room temperature. For the etherification in the 1- and 3-positions, alkylating agents are employed, preferably diazomethane, dialkyl sulfate. Others are, for example, cycloalkyl halogenides and dihydropyran.

For esterification of the 17β-hydroxy group in 1,3(16)-di(tri)-esters and/or the 16- and/or 17-hydroxy group in 1,3-diethers, the steroid is treated, for example, with an acid anhydride in the presence of a strong acid, e.g., p-toluenesulfonic acid, $HClO_4$, or pyridine/acid anhydride, optionally with heating. The last-mentioned methods can also be used to convert the free hydroxy compounds directly into tri- and tetraacylates. 1,3,16-Triesters and 1,3-diethers can be converted into the corresponding 16- and/or 17-tetrahydropyranyl esters with dihydropyran in the presence of a strong acid, e.g., p-toluenesulfonic acid. The etherification of the 16- and/or 17-OH-group in the 1,3-diethers of this invention having an alkyl residue is preferably conducted with an alkyl halogenide in liquid ammonia.

The free OH-groups can be liberated from 1,3-diacyl-17-tetrahydropyranyl derivatives and from 1,3,16-triacyl-17-tetrahydropyranyl derivatives by alkaline saponification.

The optional subsequent etherification of compounds with free hydroxy groups in the 16- and 17-positions can also be conducted by conventionally condensing, in the presence of a strong acid, a 16,17-dihydroxy-8α-estratriene of general Formula Ia

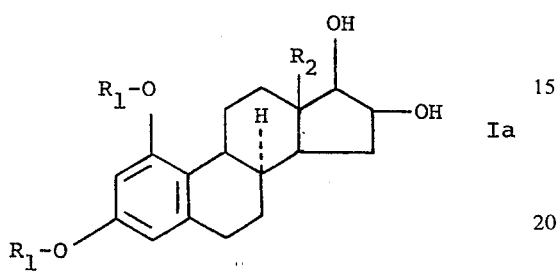

wherein the hydroxy groups can be in the 16α,17α- or 16β,17β-position and $R_1$ and $R_2$ have the values given above, with a carbonyl compound of Formula III

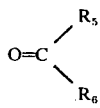

wherein $R_5$ and $R_6$ have the values given above.

In the condensation of the 16,17-diol with the carbonyl compound according to the process of this invention, the carbonyl compound generally serves both as the condensation agent and as the solvent. However, it is also possible to conduct the reaction in the presence of an additional inert solvent, diluent, or solubilizer, such as, for example, dioxane, tetrahydrofuran, glyme or diglyme. Carbonyl compounds suitable for this condensation process are especially: formaldehyde, acetaldehyde, acetone, methyl ethyl ketone, methyl butyl ketone, ethyl butyl ketone, acetophenone, benzophenone, methyl benzyl ketone, benzaldehyde, p-fluoroacetophenone, p-chloroacetophenone, p-hydroxyacetophenone and like compounds. Catalysts for the desired condensation are strong acids, especially Lewis acid, e.g., concentrated hydrochloric acid, sulfuric acid, p-toluenesulfonic acid, perchloric acid, boron trifluoride etherate, and like compounds. In general, a few drops of these catalytically active acidic compounds are sufficient to catalyze the reaction in the desired manner. The condensation generally occurs under very gentle reaction conditions. Normally, room temperature or a slightly elevated reaction temperature and a reaction time of about 1–8 hours are sufficient.

An ether splitting step is conducted according to conventional methods. Examples of such processes are the splitting with pyridine hydrochloride or pyridine-concentrated hydrochloric acid at an elevated temperature (180°–220° C.), or with a hydrohalic acid in the presence of a lower carboxylic acid at temperatures of below 150° C. The splitting of tetrahydropyranyl ethers occurs under gentle conditions by adding an acid.

In general, enol acylates are used as the starting compounds wherein $R_1$ has the value desired for the final product. However, to increase the yield, it can be advantageous to start with compounds wherein the hydroxy groups in the 1- and 3-positions are esterified or etherified, e.g., with other easily replaceable groups.

The 8α-estratrienes of general Formula I having a hydroxy group in the 16α- or 17α-positions can also be obtained by treating a tetraene of the general Formula IV

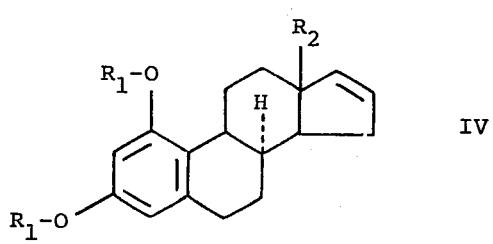

wherein $R_1$ and $R_2$ have the values given above, with osmium tetroxide, and splitting the thus-obtained osmate by reduction.

The 8α-estratrienes of general Formula I having a hydroxy group in the 16α- and 17β-, or 16β- and 17α-positions can also be produced by converting a tetraene of the general Formula IV into the corresponding 16,17-epoxide and subsequently opening the oxirane ring of the thus-produced epoxide.

The reaction of the tetraene of Formula IV with osmium tetroxide and the reductive splitting of the osmate, for example with an aqueous solution of mannitol, sodium bisulfite, or with lithium hydridoaluminate, is conducted in a conventional manner.

The reaction of the tetraene of Formula IV to the epoxide and the subsequent opening of the oxirane ring are also effected in accordance with known methods. The epoxide can be prepared, for example, by reaction of the tetraene of Formula IV with a peracid, e.g., perbenzoic acid, m-chloroperbenzoic acid or peracetic acid, or by conversion of the tetraene of Formula IV to a halohydrin, e.g., by reaction with hypobromous acid to the bromohydrin, and subsequent ring closure with an alkali, e.g., potassium hydroxide solution. The oxirane ring can be opened by acidic hydrolysis, e.g., in the presence of sulfuric acid, perchloric acid, or by reaction with a metal hydride, e.g., lithium hydridoaluminate and sodium hydridoborate.

The 16,17-dihyroxy compounds optionally can be converted, by subsequent esterification or etherification, into desired esterified or etherified products of Formula I.

The starting compounds can be produced, for example, as will be described hereinbelow, using rac.-1,3,17-triacetoxy-8α-estra-1,3,5(10),16-tetraene (A); optically active 1,3,17-triacetoxy-8α-estra-1,3,5(10),16-tetraene (B); and 1,3-diacetoxy-8α-estra-1,3,5(10),16- tetraene (C).

PREPARATIONS

A:

rac.-1,3,17-Triacetoxy-8α-estra-1,3,5(10),16-tetraene

A trace of iodine and 2 ml. of ethyl bromide are added to a suspension of 17 g. of Mg filings in 15 ml. of absolute THF; after heating to 50° C., vinyl chloride is gradually introduced into the reaction mixture until the temperature has dropped to room temperature. During this step, 250 ml. of absolute THF is added dropwise. At 20° C., a solution of 52.4 g. of 6,8-dimethoxytetralone in 84 ml. of absolute THF and 82 ml. of absolute benzene is gradually introduced dropwise into this vinyl Grignard solution, and the mixture is allowed to stand overnight in a refrigerator under $N_2$. After warming to room temperature, the batch is introduced into a mixture of 84 ml. of glacial acetic acid and 350 ml. of ice water, further agitated for 30 minutes, and the aqueous phase is separated and extracted with benzene. The combined organic extracts are washed neutral with $NaHCO_3$ solution and water and dried. This solution of the vinol compound is combined with 38 g. of 2-methylcyclopentanedione-(1,3) and 160 mg. of potassium hydroxide (pulverized), concentrated to half its volume, and 170 ml. of methanol is gently added dropwise thereto, whereupon the mixture is heated for 3 hours under $N_2$ to the boiling point. Then, the mixture is allowed to cool to room temperature, diluted with ether, and the excess 2-methylcyclopentanedione-(1,3) is removed by extraction with 10% sodium hydroxide solution. After washing the mixture neutral with water, drying, and evaporation, the product is recrystallized from ethanol, thus obtaining 66 g. of 1,3-dimethoxy-8,14-seco-1,3,5(10),9(11)-estratetraene-14,17-dione; m.p. 87/88°–89° C.

A solution of 69 g. of 1,3-dimethoxy-8,14-seco-1,3,5(10)9(11)-estratetraene-14,17-dione in 940ml. of distilled benzene is combined with 3 g. of p-toluenesulfonic acid and heated for 20 minutes to the boiling point. After cooling, the mixture is extracted with cold $NaHCO_3$ solution, washed neutral with water, and dried. After recrystallization from acetone/hexane over carbon, 60 g. of rac.-1,3-dimethoxy-1,3,5(10),8,14-estrapentaen-17-one is produced; m.p. 120°–121° C.

0.120 mg. of rac.-1,3-dimethoxy-1,3,5(10),8,14-estrapentaen-17-one in 40 ml. of THF is hydrogenated in the presence of 60 mg. of palladium/$CaCO_3$ (5%) at room temperature under a hydrogen pressure of 50 atmospheres gauge within 17 hours. Thereafter, the reaction product is filtered off from the catalyst, the filtrate is evaporated, and the residue is recrystallized from methanol, thus obtaining 20 mg. rac.-1,3-dimethoxy-8α-estra-1,3,5(10)-trien-17-one; m.p. 158/59°–160° C.

A mixture of 25 g. of pyridine-hydrochloride and 2.5 g. of rac.-1,3-dimethoxy-8α-estra-1,3,5(10)-trien-17-one is heated under $N_2$ and agitation for 3 hours to 200° C. After cooling, adding 120 ml. of pyridine and 12 ml. of acetic anhydride, and 1 hour of agitation at room temperature, the solution is introduced into ice water/NaCl, stirred for one-half hour, filtered off, and worked up. The crude product (2.5 g.) is purified by gradient chromatography (60 g. of $SiO_2$; methylene chloride/10% acetone), thus producing, after recrystallization from methanol, 710 mg. of rac.-1,3-diacetoxy-8α-estra-1,3,5(10)-trien-17-one; m.p. 179°–180.5° C.

A mixture of 5 g. of rac.-1,3-diacetoxy-8α-estra-1,3,5(10)-trien-17-one, 100 ml. of isopropenyl acetate, and 14.4 g. of p-toluenesulfonic acid is heated for 21 hours under a slight $N_2$ stream to 105° C. After the mixture has been heated to 125° C., 50 ml. of isopropenyl acetate are gradually distilled off. After cooling, 10 ml. of pyridine is added, the mixture is diluted with methylene chloride, washed with saturated sodium bicarbonate solution and water, and dried over sodium sulfate. The solvent is evaporated under vacuum. After chromatography on 260 g. of $SiO_2$, 3 g. of oily rac.-1,3,17-triacetoxy-8α-estra-1,3,5(10),16-tetraene is obtained, which is further processed as the crude product.

With the use of 2-ethylcyclopentanedione-(1,3) and 2-propylcyclopentanedione-(1,3), respectively, the following products are obtained after the reaction mixtures have been worked up as set forth in (A):

rac.-1,3,17-triacetoxy-18-methyl-8α-estra-1,3,5(10),16-tetraene rac.-1,3,17-triacetoxy-18-ethyl-8α-estra-1,3,5(10),16-tetraene.

With the use of isopropenyl butyrate in place of isopropenyl acetate in the last stage, the following compound is obtained:

rac.-1,3,17-triacetoxy-17-butyryloxy-8α-estra-1,3,5(10),16-tetraene.

B: opt.

act.-1,3,17-Triacetoxy-8α-estra-1,3,5(10),16-tetraene

A suspension of 42 g. of 3-hydroxy-8α-estra-1,3,5(10)-trien-17-one in 600 ml. of glacial acetic acid is combined with 120 g. of lead tetraacetate; then, the mixture is agitated for 3 minutes at room temperature under the exclusion of moisture and thereafter poured into 600 ml. of ice water. The precipitate is vacuum-filtered, washed with water, and the filter residue is taken up in methylene chloride. The solution of the substance is washed neutral with sodium bicarbonate solution and water, dried, and concentrated. The concentrate is filtered with methylene chloride over 400 g. of silica gel (+ 10% of water). The fractions containing the substance are combined and freed of solvent, thus obtaining 7 g. of 8α-estra-1,4-diene-10β-acetoxy-3,17-dione, which is further processed as the crude product.

A solution of 13.0 g. of 8α-estra-1,4-diene-10β-acetoxy-3,17-dione in 235 ml. of acetic anhydride is mixed dropwise with 0.7 ml. of concentrated sulfuric acid and agitated for 3 hours at room temperature, during which time the substance is gradually dissolved. The charge is then introduced into ten times the amount of ice water to which is added 7 g. of sodium carbonate; the mixture is agitated for 1 hour and then filtered off. The washed and dried residue is recrystalized from methanol/methylene chloride, thus obtaining 7 g. of 1,3-diacetoxy-8α-estra-1,3,5(10)-trien-17-one, m.p. 208°–211° C. $[\alpha]_D^{20} = +89°$ ($CHCl_3$; c = 0.5).

A mixture of 5 g. of 1,3-diacetoxy-8α-estra-1,3,5(10)-trien-17-one, 100 ml. of isopropenyl acetate, and 14.4 g. of p-toluenesulfonic acid is heated for 21 hours to 105° C. under a slight $N_2$ stream. After heating to 125° C., 50 ml. of iospropenyl acetate is gradually distilled off. After cooling, 10 ml. of pyridine is added, the mixture is diluted with methylene chloride, washed with saturated sodium bicarbonate solution and water, and dried over sodium sulfate. The solvent is evaporated under vacuum. After chromatography on 260 g. of $SiO_2$, 3 g. of 1,3,17-triacetoxy-8α-estra- 1,3,5(10),16-tetraene is obtained as an oil, which is further processed in the form of the crude product.

Analogously, the following compound is obtained: opt. act.-1,3,17-triacetoxy-18-methyl-8α-estra-1,3,5(10),16-tetraene.

C: opt. act.-1,3-Diacetoxy-8α-estra-1,3,5(10),16-tetraene

Two grams of 1,3-dimethoxy-8α-estra-1,3,5(10)-trien-17-one is added to a solution of 3.4 g. of tosylhydrazine in 80 ml. of methanol and heated to the boiling point for 4 hours. After cooling and crystallization of the substance, the precipitate is filtered from 1,3-dimethoxy-17-tosylhydrazono-8α-estra-1,3,5(10)-triene, the latter being suspended in 40 ml. of absolute ether. The suspension is combined dropwise under agitation with an ether - methyllithium solution. After 2 hours, the mixture is gently decomposed with water, extracted with ether, washed neutral with water, dried, and evaporated.

The residue of 1,3-dimethoxy-8α-estra-1,3,5(10),16-tetraene is heated with 20 g. of pyridine hydrochloride under $N_2$ and agitation for 3 hours to 200° C. After cooling, 80 ml. of pyridine and 8 ml. of acetic anhydride are added thereto, and the mixture is agitated for 1 hour at room temperature under $N_2$, whereupon it is precipitated into ice water and filtered off. The substance is taken up in methylene chloride, the solution is washed neutral with water, dried, and evaporated, thus obtaining 1,3-diacetoxy-8α-estra-1,3,5(10),16-tetraene.

The following examples will serve to explain the invention.

The compounds of this invention are obtained as racemates and also as enantiomers. It is readily apparent to a person skilled in the art that the racemates can be separated into the enantiomers by separation methods generally known for the separation of optical antipodes. Therefore, the invention includes racemates and enantiomers.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Two grams of rac.-1,3,17-triacetoxy-8α-estra-1,3,5(10),16-tetraene is epoxidized in 70 ml. of methylene chloride with the addition of 3 g. of sodium sulfate (dried), 0.36 g. of sodium acetate, and 2.2 ml. of stabilized peracetic acid at room temperature within 2 hours. The reaction mixture is washed neutral at the freezing point with water, sodium carbonate solution, and water, and then dried over sodium sulfate. After filtration, the solvent is removed by evaporation. The remaining residue of 1.5 g. of rac.-1,3,17β-triacetoxy-16α,17α-epoxy-8α-estra-1,3,5(10)-triene is reacted without further purification as set forth in Example 2.

Analogously, the following compounds are obtained:
rac.-1,3,17β-triacetoxy-16α,17α-epoxy-18-methyl-8α-estra-1,3,5(10)-triene
rac.-1,3,17β-triacetoxy-16α,17α-epoxy-18-ethyl-8α-estra-1,3,5(10)-triene.

EXAMPLE 2

500 mg. of rac.-1,3,17β-triacetoxy-16α,17α-epoxy-8α-estra-1,3,5(10)-triene is suspended in 50 ml. of methanol and mixed with 10 ml. of 5N sulfuric acid. After 15 hours of agitation, the substance is dissolved. The solution is concentrated with the use of a forced circulation evaporator, the concentrate is introduced into ice-cold saturated sodium chloride solution, the precipitate is filtered off, taken up in ethyl acetate, and washed neutral with sodium chloride solution. After recrystallization from acetone/hexane, 175 mg. of rac.-1,3,16α-trihydroxy-8α-estra-1,3,5(10)-trien-17-one is obtained.

Analogously, the following substances are produced:
rac.-1,3,16α-trihydroxy-18-methyl-8α-estra-1,3,5(10)-trien-17-one
rac.-1,3,16α-trihydroxy-18-ethyl-8α-estra-1,3,5(10)-trien-17-one.

EXAMPLE 3

150 mg. of rac.-1,3,16α-trihydroxy-8α-estra-1,3,5(10)-trien-17-one is taken up in 20 ml. of pyridine and combined with 10 ml. of acetic anhydride. After 5 hours of agitation at room temperature, the mixture is introduced into ice water, the precipitate is filtered off and taken up in ether. The ether solution is washed neutral with saturated sodium chloride solution, dried, and evaporated. Recrystallization from methanol yields 100 mg. of rac.-1,3,16α-triacetoxy-8α-estra-1,3,5(10)-trien-17-one.

Analogously, the following compounds are obtained:
rac.-1,3,16α-triacetoxy-18-methyl-8α-estra-1,3,5(10)-trien-17-one. rac.-1,3,16α-triacetoxy-18-ethyl-8α-estra-1,3,5(10)-trien-17-one.

By the use of caproic anhydride and enanthic anhydride, respectively, in place of acetic anhydride, the following substances are produced:
rac.-1,3,16α-tris(hexanoyloxy)-8α-estra-1,3,5(10)-trien-17-one
rac.-1,3,16α-tris(heptanoyloxy)-8α-estra-1,3,5(10)-trien-17-one.

EXAMPLE 4

500 mg. of rac.-1,3,17β-triacetoxy-16α,17α-epoxy-8α-estra-1,3,5(10)-triene is isomerized with 16 g. of silica gel in 25 ml. of methylene chloride at room temperature within 25 hours, yielding 400 mg. of rac.-1,3,16α-triacetoxy-8α-estra-1,3,5(10)-trien-17-one.

EXAMPLE 5

A mixture of 3 g. of rac.-1,3,16α-trihydroxy-8α-estra-1,3,5(10)-trien-17-one in 300 ml. of ethyl acetate and 25 ml. of acetic anhydride is combined with 0.15 ml. of perchloric acid (70%). After 5 minutes of agitation at room temperature, 25 ml. of pyridine is added. The mixture is concentrated in a forced circulation evaporator, the residue is precipitated into ice water/NaCl, stirred for 30 minutes to decompose the excess acetic ahydride, and filtered off. The precipitate is taken up in ether, the solution is washed with saturated sodium chloride solution, dried, and evaporated, thus obtaining 1.5 g. of rac.-1,3,16α-triacetoxy-8α-estra-1,3,5(10)-trien-17-one.

Analogously, the following compounds are produced:
rac.-1,3,16α-triacetoxy-18-methyl-8α-estra-1,3,5(10)-trien-17-one rac.-1,3,16α-tris(heptanoyloxy)-8α-estra-1,3,5(10)-trien-17-one.

EXAMPLE 6

500 mg. of rac.-1,3,17β-triacetoxy-16α,17α-epoxy-8α-estra-1,3,5(10)-triene is added dropwise in 10 ml. of THF to a suspension of 500 mg. of lithium tetrahydridoaluminate in 15 ml. of absolute THF under ice cooling. After 1 hour of agitation at room temperature, 10 ml. of glacial acetic acid is gently added thereto. The solution is diluted with ether and, at the freezing temperature, washed neutral successively with dilute hydrochloric acid, dilute sodium bicarbonate solution, and saturated sodium chloride solution, and then worked up. A mixture of 240 mg. of rac.-8α-estra-1,3,5(10)-triene-1,3,16α,17β-tetrol and 60 mg. of rac.-8α-estra-1,3,5(10)-triene-1,3,16α,17α-tetrol.

EXAMPLE 7

500 mg. of rac.-1,3,16α-triacetoxy-8α-estra-1,3,5(10)-trien-17-one is added dropwise under ice cooling in 10 ml. of THF to a suspension of 500 mg. of lithium tetrahydridoaluminate in 15 ml. of absolute THF. After 1 hours of agitation at room temperature, 10 ml. of glacial acetic acid is gently added. The solution is diluted with ether and washed neutral at the freezing temperature successively with dilute hydrochloric acid, dilute sodium bicarbonate solution, and saturated sodium chloride solution, and then the mixture is worked up, thus obtaining 300 mg. of rac.-8α-estra-1,3,5(10)-triene-1,3,16α,17β-tetrol.

Analogously, the following are obtained:
rac.-18-methyl-8α-estra-1,3,5(10)-triene-1,3,16α,17β-tetrol
rac.-18-ethyl-8α-estra-1,3,5(10)-triene-1,3,16α,17β-tetrol.

EXAMPLE 8

Two grams of rac.-1,3,17-triacetoxy-8α-estra-1,3,5(10),16-tetraene is agitated in 40 ml. of glacial acetic acid and 2 ml. of acetic anhydride with 5.5 g. of lead tetraacetate for 15 hours at room temperature. The mixture is evaporated in a forced circulation evaporator. The residue is taken up in ethyl acetate and washed neutral with saturated sodium chloride solution. By preparative thin-layer chromatography, minor amounts of starting material are separated. After elution with acetone, the mixture is afteracetylated with acetic anhydride and pyridine. After working up the reaction mixture and recrsytallization from methylene chloride/isopropyl ether, 700 mg. of rac.-1,3,16β-triacetoxy-8α-estra-1,3,5(10)-trien-17-one is obtained.

Analogously, the following compound is obtained:
rac.-1,3,16β-trihydroxy-18-methyl-8α-estra-1,3,5(10)-trien-17-one.

EXAMPLE 9

500 mg. of rac.-1,3,16β-triacetoxy-8α-estra-1,3,5(10)-trien-17-one is added dropwise in 10 ml. of THF to a suspension of 500 mg. of lithium aluminum hydride in 15 ml. of THF under ice cooling. After 1 hour of agitation at room temperature, 10 ml. of glacial acetic acid is gently added thereto. The solution is diluted with ether and at the freezing temperature washed neutral successively with dilute hydrochloric acid, dilute sodium bicarbonate solution and saturated sodium chloride solution. After the mixture has been worked up, 250 mg. of rac.-8α-estra-1,3,5(10)-triene-1,3,16β,17β-tetrol.

Analogously, rac.-18-methyl-8α-estra-1,3,5(10)-triene-1,3,16β,17β-tetrol is obtained.

EXAMPLE 10

A mixture of 2 g. of rac.-8α-estra-1,3,5(10)-triene-1,3,16α,17β-tetrol in 200 ml. of ethyl acetate and 15 ml. of acetic anhydride is combined with 0.1 ml. of 70% perchloric acid. After 5 minutes of agitation, 20 ml. of pyridine is added thereto. The mixture is worked up in accordance with Example 5; yield: 700 mg. of rac.-1,3,16α,17β-tetraacetoxy-8α-estra-1,3,5(10)-triene.

EXAMPLE 11

100 mg. of rac.-8α-estra-1,3.5(10)-triene-1,3,16β,17β-tetrol is taken up in 15 ml. of pyridine and combined with 7.5 ml. of acetic anhydride. After 5 hours of agitation at room temperature, the mixture is worked up according to Example 3. Yield: 65 mg. of rac.-1,3,16β,17β-tetraacetoxy-8α-estra-1,3,5(10)-triene.

EXAMPLE 12

One gram of 1,3,17-triacetoxy-8α-estra-1,3,5(10),16-tetraene is epoxidized in 35 ml. of methylene chloride with the addition of 1.5 g. of sodium sulfate (dried), 0.2 g. of sodium acetate, and 1.1 ml. of stabilized peracetic acid at room temperature within 2 hours. The reaction mixture is washed neutral at the freezing temperature with water, sodium carbonate solution, and water, and then dried over sodium sulfate. After filtration, the solvent is evaporated. The remaining residue [0.5 g. of opt. act.-1,3,17β-triacetoxy-16α,17α-epoxy-8α-estra-1,3,5(10)-triene] is reacted according to Example 13 without any further purification.

EXAMPLE 13

500 mg. of 1,3,17β-triacetoxy-16α,17α-epoxy-8α-estra-1,3,5(10)-triene is isomerized with 15 g. of silica gel in 25 ml. of methylene chloride at room temperature in 3 hours, thus obtaining 350 mg. of opt. act.-1,3,16α-treacetoxy-8α-estra-1,3,5(10)-trien-17-one, m.p. 230°–237° C. (methanol/acetone).

EXAMPLE 14

One gram of opt. act.-1,3,17-triacetoxy-8α-estra-1,3,5-(10),16-tetraene is agitated at room temperature for 15 hours in 20 ml. of glacial acetic acid and 1 ml. of acetic anhydride with 2.7 g. of lead tetraacetate. The mixture is evaporated in a forced circulation evaporator. The residue is taken up in ethyl acetate and washed neutral with saturated sodium chloride solution. By preparative thin-layer chromatography, minor amounts of starting compound are separated. After elution with acetone, the mixture is after-acetylated with acetic anhydride and pyridine. The mixture is worked up and recrystallized from methylene chloride/isopropyl ether, thus obtaining 700 mg. of opt. act.-1,3,16β-triacetoxy-8α-estra-1,3,5(10)-trien-17-one, m.p. 220°–224° C. (methanol/acetone).

EXAMPLE 15

A Grignard solution is prepared from 5.6 g. of Mg filings and 15.7 ml. of ethyl bromide in 78 ml. of absolute THF and added dropwise under ice cooling to 94 ml. of a saturated solution of acetylene in absolute THF. Acetylene is furthermore introduced into the mixture for another hour at room temperature, and then a solution of 1.4 g. of 1,3,16α-triacetoxy-8α-estra-1,3,5(10)-trien-17-one in 60 ml. of absolute THF is added dropwise at room temperature, whereupon the mixture is stirred for another 20 hours under $N_2$ at 70° C. Then, the mixture is decomposed with saturated ammonium chloride solution and extracted with ether. The ether solution is washed neutral successively with ammonium chloride solution and water, dried, and evaporated. The residue is dissolved, for after-acetylation, in 20 ml. of pyridine, combined with 10 ml. of acetic anhydride, and allowed to stand for 5 hours at room temperature. After the mixture has been poured into ice water and worked up, the crude product is purified by chromatography on silica gel, thus producing 500 mg. of 1,3,16α-triacetoxy-17α-ethinyl-8α-estra-1,3,5(10)-trien-17β-ol as an amorphous powder. $[\alpha]_D^{20} = +23.6°$ ($CHCl_3$).

EXAMPLE 16

A solution of 475 mg. of estra-1,3,5(10)-triene-1,3,16α,17β-tetrol and 0.6 ml. of dimethyl sulfate in 2.5 ml. of acetone is gradually added to a boiling suspension of 1.4 g. of $K_2CO_3$ in 5 ml. of acetone. After heating the mixture for 4 hours under reflux, it is introduced into ice water, agitated for 1 hour, filtered, and worked up. After chromatographic purification on silica gel, 1,3-dimethoxy-8α-estra-1,3,5(10)-triene-16α,17β-diol is thus produced.

EXAMPLE 17

A solution of 900 mg. of 1,3-dimethoxy-8α-estra-1,3,5(10)-triene-16α,17β-diol in 45 ml. of absolute benzene is combined with 1.35 ml. of distilled dihydropyran and 10 mg. of p-toluenesulfonic acid. The solution is agitated for 1.5 hours at room temperature, then washed neutral with a sodium bicarbonate solution and water, dried, and evaporated, thus producing 800 mg. of 1,3-dimethoxy-16α,17β-bis(tetrahydropyranyloxy)-8α-estra-1,3,5(10)-triene.

EXAMPLE 18

A solution of 500 mg. of 1,3,16α-triacetoxy-8α-estra-1,3,5(10)-trien-17-one in 20 ml. of methanol is combined with 10 ml. of 0.1N sodium hydroxide solution and agitated for 4 hours at room temperature under $N_2$. The mixture is then diluted with ethyl acetate, washed neutral with water, dried, and evaporated, thus obtaining 1,3,17β-trihydroxy-8α-estra-1,3,5(10)-trien-16-one.

EXAMPLE 19

A solution of 1.38 g. of 1,3-diacetoxy-8α-estra-1,3,5(10),16-tetraene and 1.0 g. of osmium tetroxide in 15 ml. of pyridine is agitated for 2 hours at room temperature. Then a solution of 1.8 g. of sodium bisulfite in 30 ml. of water and 20 ml. of pyridine is added thereto under agitation. The mixture is stirred for 10 minutes and extracted with methylene chloride. The methylene chloride solution is dried and evaporated. The residue is dissolved in 5 ml. of pyridine and heated with 3 ml. of acetic anhydride on a steam bath for 30 minutes. The mixture is then poured into ice water, worked up, dried, and evaporated, thus obtaining 1,3,16α,17α-tetraacetoxy-8α-estra-1,3,5(10)-triene.

EXAMPLE 20

A solution of 350 mg. of 1,3-diacetoxy-8α-estra-1,3,5(10),16-tetraene in 15 ml. of ether is combined with 7 ml. of a 12% strength ether - monoperphthalic acid solution. After allowing the mixture to stand at room temperature for 7.5 hours, the mixture is worked up, yielding 1,3-diacetoxy-16α,17α-epoxy-8α-estra-1,3,5(10)-triene which, in the form of the crude product, is heated to the boiling point with 30 ml. of glacial acetic acid for 2–3 hours. After concentration under vacuum, the residue is heated, for purposes of esterification, with 2 ml. of pyridine and 2 ml. of acetic anhydride for 1.5 hours on a steam bath under $N_2$. After the mixture has been introduced into ice water, it is taken up in methylene chloride and worked up, thus producing, after purification by chromatography on $SiO_2$, 1,3,16β,17α-tetraacetoxy-8α-estra-1,3,5(10)-triene.

EXAMPLE 21

A suspension of 330 mg. of 1,3-diacetoxy-8α-estra-1,3,5(10),16-tetraene, 10 ml. of absolute dimethyl sulfoxide, and 0.6 ml. of water is combined at about 12° C. with incremental portions of 280 mg. of N-bromosuccinimide. After 30 minutes, the reaction mixture is worked up and the residue heated for 1 hour on a steam bath with 10 ml. of 3% methanolic potassium hydroxide solution. The mixture is then neutralized with glacial acetic acid, evaporated, and worked up, thus producing 1,3-diacetoxy-16β,17β-epoxy-8α-estra-1,3,5(10)-triene which is heated to the boiling point with 5 ml. of glacial acetic acid for 3 hours. The mixture is then concentrated under vacuum, the residue is heated under $N_2$ in 3 ml. of pyridine with 3 ml. of acetic anhydride on a steam bath for 1.5 hours, introduced into ice water, and worked up. After separation by chromatography, 1,3,16α,17β-tetraacetoxy-8α-estra-1,3,5(10)-triene and 1,3,16β,17α-tetraacetoxy-8α-estra-1,3,5(10)-triene are obtained.

EXAMPLE 22

A solution of 0.95 g. of 8α-estra-1,3,5(10)-triene-1,3,16α,17β-tetrol in 30 ml. of ethanol is combined with 1.25 g. of $K_2CO_3$ and 1.4 ml. of cyclopentyl bromide. The suspension is heated to the boiling point for 5 hours under agitation and $N_2$ and, after cooling, introduced into ice water and filtered. The residue is taken up in ether, the organic phase is washed neutral, dried, and evaporated, thus obtaining after purification by chromatography 0.35 g. of 1,3-bis(cyclopentyloxy)-8α-estra-1,3,5(10)-triene-16α,17β-diol.

EXAMPLE 23

1.2 g. of 8α-estra-1,3,5(10)-triene-1,3,16α,17α-tetrol is dissolved in 50 ml. of acetone; the solution is mixed with 50 mg. of p-toluenesulfonic acid and stirred for 1 hour at room temperature. The mixture is then combined with 2 ml. of pyridine, diluted with ethyl acetate, and washed neutral with saturated sodium chloride solution. After drying and evaporation, 1.1 g. of 16α,17α-isopropylidenedioxy-8α-estra-1,3,5(10)-triene-1,3-diol is obtained.

EXAMPLE 24

300 mg. of 16α,17α-isopropylidenedioxy-8α-estra-1,3,5(10)-triene-1,3-diol is dissolved in 10 ml. of pyridine, mixed with 10 ml. of acetic anhydride, and allowed to stand for 16 hours at room temperature. The mixture is then introduced into ice water, extracted with ether, the ether phase washed with water so that it is neutral, and then dried and evaporated. After purification by layer chromatography on silica gel, 200 mg. of 1,3-diacetoxy-16α,17α-isopropylidenedioxy-8α-estra-1,3,5(10)-triene is produced.

EXAMPLE 25

A solution of 0.9 g. of 16α,17α-isopropylidenedioxy-8α-estra-1,3,5(10)-triene-1,3-diol and 0.83 ml. of dimethyl sulfate in 5 ml. of acetone (pro analysis) is gradually added dropwise to a boiling suspension of 2.9 g. of potassium carbonate in 10 ml. of acetone. After heating the mixture for 4 hours under reflux, the mixture is introduced into ice water and extracted with ether. The organic phase is washed, dried, and evaporated, thus obtaining, after purification by chromatography over silica gel, 1,3-dimethoxy-16α,17α-isopropylidenedioxy-8α-estra-1,3,5(10)-triene.

EXAMPLE 26

0.6 g. of 8α-estra-1,3,5(10)-triene-1,3,16α,17α-tetrol is dissolved in 10 ml. of acetophenone (pro analysis), mixed with 0.1 ml. of 70% perchloric acid, and agitated for 3 hours at room temperature. After the addition of 0.5 ml. of pyridine, the mixture is diluted with ether and washed neutral. After evaporation, the acetophenone is eliminated by steam distillation, and the residue is again taken up in ether; the ether solution is dried and evaporated. After purification by layer chromatography on silica gel, 16α,17α-(1'-methyl-1'-phenylmethylenedioxy)-8α-estra-1,3,5(10)-triene-1,3-diol is obtained.

EXAMPLE 27

200 mg. of 16α,17α-(1'-methyl-1'-phenylmethylenedioxy)-8α-estra-1,3,5(10)-triene-1,3-diol is reacted in pyridine with acetic anhydride analogously to Example 2, yielding 120 mg. of 16α,17α-(1'-methyl-1'-phenylmethylenedioxy)-1,3-diacetoxy-8α-estra-1,3,5(10)-triene.

EXAMPLE 28

350 mg. of 16α,17α-(1'-methyl-1'-phenylmethylenedioxy)-8α-estra-1,3,5(10)-triene-1,3-diol is reacted with dimethyl sulfate in the presence of potassium carbonate analogously to Example 25, producing 200 mg. of 1,3-dimethoxy-16α,17α-(1'-methyl-1'-phenylmethylenedioxy)-8α-estra-1,3,5(10)-triene.

EXAMPLE 29

0.8 g. of 8α-estra-1,3,5(10)-triene-1,3,16β,17β-tetrol is dissolved in 40 ml. of acetone and reacted to the acetonide analogously to Example 23. After chromatographic purification, 0.6 g. of 16β,17β-isopropylidenedioxy-8α-estra-1,3,5(10)-triene-1,3-diol is obtained.

EXAMPLE 30

0.5 g. of 16β,17β-isopropylidenedioxy-8α-estra-1,3,5(10)-triene-1,3-diol is acetylated with acetic ahydride in pyridine analogously to Example 24, thus obtaining 375 mg. of 16β,17β-isopropylidenedioxy-1,3-diacetoxy-8α-estra-1,3,5(10)-triene.

EXAMPLE 31

0.4 g. of 16β,17β-isopropylidenedioxy-8α-estra-1,3,5(10)-triene-1,3-diol is reacted analogously to Example 25 with dimethyl sulfate and potassium carbonate in acetone, yielding 0.2 g. of 1,3-dimethoxy-16β,17β-isopropylidenedioxy-8α-estra-1,3,5(10)-triene.

EXAMPLE 32

A solution of 900 mg. of 16β,17β-isopropylidenedioxy-8α-estra-1,3,5(10)-triene-1,3-diol in 45 ml. of absolute benzene is combined with 1.35 ml. of distilled dihydropyran and 10 mg. of p-toluenesulfonic acid. The solution is agitated for 16 hours at room temperature, then washed neutral with a sodium bicarbonate solution and water, dried, and evaporated, yielding 850 mg. of 16β,17β-isopropylidenedioxy-1,3-bis(tetrahydropyranyloxy)-8α-estra-1,3,5(10)-triene.

EXAMPLE 33

0.5 g. of 16β,17β-isopropylidenedioxy-8α-estra-1,3,5(10)-triene-1,3-diol is dissolved in 5 ml. of pyridine and warmed to 50° C. with 5 ml. of enanthic anhydride for 2 hours. Thereafter, 25 ml. of water is added under stirring and cooling. After 1 hour of agitation, the mixture is taken up in ether. The organic phase is washed successively with dilute sulfuric acid, $Na_2CO_3$ solution, and water, dried, and evaporated, thus obtaining, after purification by chromatography over silica gel, 16β,17β-isopropylidenedioxy-1,3-bis(heptanoyloxy)-8α-estra-1,3,5(10)-triene as an oil.

EXAMPLE 34

400 mg. of 16α,17α-isopropylidenedioxy-8α-estra-1,3,5(10)-triene-1,3-diol is dissolved in 6 ml. of pyridine, combined with 4 ml. of valeric acid anhydride, and heated to 160° C. under $N_2$ and agitation for 8 hours. The mixture is then cooled, water is added dropwise under cooling (25 ml.), and the mixture is stirred for 1 hour to decompose the anhydride. Thereafter, the oily product is taken up in ether, the solution is washed successively with dilute sulfuric acid, water, $Na_2CO_3$ solution, and water, dried, and concentrated by evaporation. After purification over silica gel, 16α,17α-isopropylidenedioxy-1,3-bis(valeryloxy)-8α-estra-1,3,5(10)-triene is obtained in the form of an oil.

EXAMPLE 35

240 mg. of 16α,17α-isopropylidenedioxy-8α-estra-1,3,5(10)-triene-1,3-diol is heated to the boiling point in 10 ml. of ethanol under $N_2$ with 1.0 ml. of cyclopentyl bromide and 1 g. of potassium carbonate for 5 hours. After precipitation into ice water, the mixture is taken up in ether, the organic phase is washed, dried, and evaporated. Chromatographic purification on silica gel yields 16α,17α-isopropylidenedioxy-1,3-bis(cyclopentyloxy)-8α-estra-1,3,5(10)-triene.

EXAMPLE 36

1,3,16α-Tris(mesyloxy)-8α-estra-1,3,5(10)-trien-17-one

A solution of 400 mg. of 1,3,16α-trihydroxy-8α-estra-1,3,5(10)-trien-17-one in 5 ml. of pyridine is combined at 0° C. with 1.5 ml. of methanesulfonic acid chloride and agitated for 3 days at 0°–10° C. The mixture is thereafter introduced inyo ice water (acidified with HCl), filtered off, and the residue is dissolved in methylene chloride. After chromatography on $SiO_2$, 250 mg. of 1,3,16α-tris(mesyloxy)-8α-estra-1,3,5(10)-trien-17-one is obtained.

19

Analogously, the following compound is produced: 1,3,16β-tris(mesyloxy)-8α-estra-1,3,5(10)-trien-17-one from 1,3,16β-trihydroxy-8α-estra-1,3,5(10)-trien-17-one.

EXAMPLE 37 rac.-1,3,16α,17β-Tetrakis(mesyloxy)-8α-estra-1,3,5(10)-triene

A solution of 400 mg. of 8α-estra-1,3,5(10)-triene-1,3,16α,17β-tetrol in 5 ml. of pyridine is combined at 0° C. with 2 ml. of methanesulfonic acid chloride, and the mixture is agitated for 3 days at 0°–10° C. Thereafter, the mixture is introduced into ice water (acidified with HCl), filtered off, and the residue dissolved in methylene chloride. After purification by chromatography on SiO$_2$, 220 mg. of rac.-1,3,16α,17β-tetrakis(mesyloxy)-8α-estra-1,3,5(10)-triene is obtained.

Analogously, 1,3,16β,17β-tetrakis(mesyloxy)-8α-estra-1,3,5(10)-triene is obtained from 8α-estra-1,3,5(10)-triene-1,3,16β,17β-tetrol; and 1,3,16β,17α-tetrakis(mesyloxy)-8α-estra-1,3,5(10)-triene is obtained from 8α-estra-1,3,5(10)-triene-1,3,16β,17α-tetrol.

EXAMPLE 38

1,3,16α-Tris(diethylaminosulfonyloxy)-17α-ethinyl-8α-estra-1,3,5(10)-trien-17β-ol A Grignard solution is produced from 5.6 g. of Mg filings and 15.7 ml. of ethyl bromide in 78 ml. of absolute tetrahydrofuran (THF); this solution is added dropwise to 94 ml. of a saturated solution of acetylene in absolute THF under ice cooling. Then, acetylene is introduced for another hour at room temperature, and thereafter a solution of 1.3 g. of 1,3,16α-triacetoxy-8α-estra-1,3,5(10)-trien-17-one in 60 ml. of absolute THF is added dropwise thereto at room temperature. The mixture is stirred for another 20 hours under N$_2$ at 70° C. Thereafter, the mixture is decomposed with saturated ammonium chloride solution and extracted with ether. The ether solution is washed neutral successively with ammonium chloride and water, dried, and evaporated. The residue (17α-ethinyl-8α-estra-1,3,5(10)-triene-1,3,16α,17β-tetrol) is dissolved in 10 ml. of dimethyl sulfoxide (DMSO), the solution is combined with 1 g. of NaH (50% suspension in paraffin oil), and agitated under nitrogen for 30 minutes at room temperature. The solution is then combined with a solution of 4 g. of diethylaminosulfonyl chloride in 8 ml. of DMSO, and the mixture is agitated for 25 hours at room temperature. The charge is then introduced into acetic ice water (NaCl) and extracted with ether. The ether phase is washed neutral with water, dried and evaporated. After purification by chromatography on SiO$_2$, the product is 500 mg. of 1,3,16α-tris(diethylaminosulfonyloxy)-17α-ethinyl-8α-estra-1,3,5(10)-trien-17β-ol.

EXAMPLE 39

1,3,16α-Tris(piperidinosulfonyloxy)-17α-ethinyl-8α-estra-1,3,5(10)-trien-17β-ol

In accordance with the process described above, 1,3,16α-tris(piperidinosulfonyloxy)-17α-ethinyl-8α-estra-1,3,5(10)-trien-17β-ol is obtained from 1,3,16α-triacetoxy-8α-estra-1,3,5(10)-trien-17-one by reaction with piperidinosulfonyl chloride.

EXAMPLE 40

1,3-Bis(mesyloxy)-16α,17α-isopropylidenedioxy-8α-estra-1,3,5(10)-triene

A solution of 500 mg. of 16α,17α-isopropylidenedioxy-8α-estra-1,3,5(10)-triene-1,3-diol in 5 ml. of pyridine is mixed with 1 ml. of methanesulfonic acid chloride at 0° C. and agitated for 3 days at 0°–10° C. Then, the mixture is introduced into ice water (acidified with HCl), filtered off, and the residue is dissolved in methylene chloride. After chromatography on SiO$_2$, 350 mg. of 1,3-bis(mesyloxy)-16α,17α-isopropylidenedioxy-8α-estra-1,3,5(10)-triene is produced.

Analogously, 1,3-bis(mesyloxy)-16β,17β-isopropylidenedioxy-8α-estra-1,3,5(10)-triene is produced from 16β,17β-isopropylidenedioxy-8α-estra-1,3,5(10)-triene-1,3-diol.

EXAMPLE 41

1,3-Bis(diethylaminosulfonyloxy)-16β,17β-isopropylidenedioxy-8α-estra-1,3,5(10)-triene A solution of 300 mg. of 16β,17β-isopropylidenedioxy-8α-estra-1,3,5(10)-triene-1,3-diol in 7 ml. of dimethyl sulfoxide (DMSO) is combined with 300 mg. of NaH (50% suspension in paraffin oil) and agitated for 30 minutes at room temperature under nitrogen. A solution of 1.2 g. of diethylaminosulfonyl chloride in 2 ml. of DMSO is then added thereto, and the mixture is allowed to stand for 25 hours at room temperature under agitation and nitrogen. The mixture is thereafter introduced into ice water, neutralized with acetic acid, and extracted with ether. The ether phase is washed neutral with water, dried, and evaporated. After purifying the residue by chromatography on SiO$_2$, 190 mg. of 1,3-bis(diethylaminosulfonyloxy)-16β,17β-isopropylidenedioxy-8α-estra-1,3,5(10)-triene is obtained.

EXAMPLE 42

1,3-Bis(pyrrolidinosulfonyloxy)-16β,17β-isopropylidenedioxy-8α-estra-1,3,5(10)-triene Analogously to Example 41, 1,3-bis(pyrrolidinosulfonyloxy)-16β,17β-isopropylidenedioxy-8α-estra-1,3,5(10)-triene is produced from 16β,17β-isopropylidenedioxy-8α-estra-1,3,5(10)-triene-1,3-diol by reaction with pyrrolidinosulfonyl chloride.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,3-oxygenated 8α-estratriene of the formula

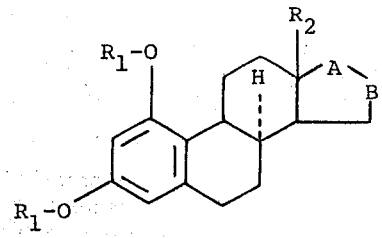

wherein —A—B— is

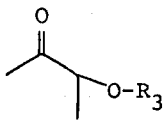 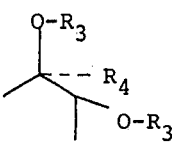 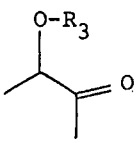 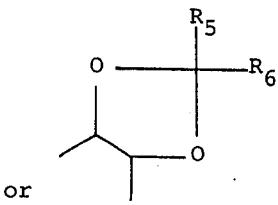

or wherein $R_1$ and $R_3$ each are a hydrogen atom, hydrocarbon acyl of 1–15 carbon atoms wherein acyl is the acyl radical of a carboxylic or sulfonic acid, alkyl of 1–5 carbon atoms, cycloalkyl of 3–8 ring carbon atoms or tetrahydropyranyl; $R_2$ is alkyl of 1–4 carbon atoms; $R_4$ is a hydrogen atom or alkyl, alkenyl or alkinyl of 1–6 carbon atoms; and $R_5$ and $R_6$ each are a hydrogen atom, alkyl of 1–5 carbon atoms, phenyl alkyl wherein alkyl is of 1–4 carbon atoms, or phenyl.

2. A compound of claim 1, wherein $R_2$ is methyl or ethyl, both $R_1$ groups are alike and each are hydrogen atoms, methyl or acetyl, $R_3$ is $R_1$ as defined herein, $R_4$ is a hydrogen atom or, when $R_3$ is hydroxy, ethinyl.

3. A compound of claim 1, 1,3,16α-trihydroxy-8α-estra-1,3,5(10)-trien-17-one.

4. A compound of claim 1, 1,3,16α-triacetoxy-8α-estra-1,3,5(10)-trien-17-one.

5. A compound of claim 1, 8α-estra-1,3,5-(10)-triene-1,3,16α,17β-tetrol.

6. A compound of claim 1, 8α-estra-1,3,5(10)-triene-1,3,16α,17α-tetrol.

7. A compound of claim 1, 1,3,16β-triacetoxy-8α-estra-1,3,5(10)-trien-17-one.

8. A compound of claim 1, 8α-estra-1,3,5(10)-trien-1,3,16β,17β-tetrol.

9. A compound of claim 1, 1,3,16α,17β-tetraacetoxy-8α-estra-1,3,5(10)-triene.

10. A compound of claim 1, 1,3,16β,17β-tetraacetoxy-8α-estra-1,3,5(10)-triene.

11. A compound of claim 1, 1,3,16α-triacetoxy-17α-ethinyl-8α-estra-1,3,5(10)-trien-17β-ol.

12. A compound of claim 1, 1,3-dimethoxy-8α-estra-1,3,5(10)-triene-16α,17β-diol.

13. A compound of claim 1, 1,3-dimethoxy-16α,17β-bis(tetrahydropyranyloxy)-8α-estra-1,3,5(10)-triene.

14. A compound of claim 1, 1,3,17β-trihydroxy-8α-estra-1,3,5(10)-trien-16-one.

15. A compound of claim 1, 1,3,16α,17α-tetraacetoxy-8α-estra-1,3,5(10)-triene.

16. A compound of claim 1, 1,3,16β,17α-tetraacetoxy-8α-estra-1,3,5(10)-triene.

17. A compound of claim 1, 1,3-bis(cyclopentyloxy)-8α-estra-1,3,5(10)-triene-16α,17β-diol.

18. A compound of claim 1, 1,3,16α-tris(mesyloxy)-8α-estra-1,3,5(10)-trien-17-one.

19. A compound of claim 1, 1,3,16β-tris(mesyloxy)-8α-estra-1,3,5(10)-trien-17-one.

20. A compound of claim 1, 1,3,16α,17β-tetrakis(mesyloxy)-8α-estra-1,3,5(10)-triene.

21. A compound of claim 1, 1,3,16β,17β-tetrakis(mesyloxy)-8α-estra-1,3,5(10)-triene.

22. A compound of claim 1, 1,3,16β,17α-tetrakis(mesyloxy)-8α-estra-1,3,5(10)-triene.

23. 1,3,16α-Tris(diethylaminosulfonyloxy)-17α-ethinyl-8α-estra-1,3,5(10)-trien-17β-ol.

24. 1,3,16α-Tris(piperidinosulfonyloxy)-17α-ethinyl-8α-estra-1,3,5(10)-trien-17β-ol.

25. A compound of claim 1, 16α,17α-isopropylidenedioxy-8α-estra-1,3,5(10)-triene-1,3-diol.

26. A compound of claim 1, 1,3-diacetoxy-16α,17α-isopropylidenedioxy-8α-estra-1,3,5(10)-triene.

27. A compound of claim 1, 1,3-dimethoxy-16α,17α-isopropylidenedioxy-8α-estra-1,3,5(10)-triene.

28. A compound of claim 1, 16α,17α-(1'-methyl-1'-phenylmethylenedioxy)-8α-estra-1,3,5(10)-triene-1,3-diol.

29. A compound of claim 1, 16α,17α-(1'-methyl-1'-phenylmethylenedioxy)-1,3-diacetoxy-8α-estra-1,3,5(10)-triene.

30. A compound of claim 1, 1,3-dimethoxy-16α,17α-(1'-methyl-1'-phenylmethylenedioxy)-8α-estra-1,3,5(10)-triene.

31. A compound of claim 1, 16β,17β-isopropylidenedioxy-8α-estra-1,3,5(10)-triene-1,3-diol.

32. A compound of claim 1, 16β,17β-isopropylidenedioxy-1,3-diacetoxy-8α-estra-1,3,5(10)-triene.

33. A compound of claim 1, 1,3-dimethoxy-16β,17β-isopropylidenedioxy-8α-estra-1,3,5(10)-triene.

34. A compound of claim 1, 16β,17β-isopropylidenedioxy-1,3-bis(tetrahydropyranyloxy)-8α-estra-1,3,5(10)-triene.

35. A compound of claim 1, 16β,17β-isopropylidenedioxy-1,3-bis(heptanoyloxy)-8α-estra-1,3,5(10)-triene.

36. A compound of claim 1, 16α,17α-isopropylidenedioxy-1,3-bis(valeryloxy)-8α-estra-1,3,5(10)-triene.

37. A compound of claim 1, 16α,17α-isopropylidenedioxy-1,3-bis(cyclopentyloxy)-8α-estra-1,3,5(10)-triene.

38. A compound of claim 1, 1,3-bis(mesyloxy)-16α,17α-isopropylidenedioxy-8α-estra-1,3,5(10)-triene.

39. A compound of claim 1, 1,3-bis(mesyloxy)-16β,17β-isopropylidenedioxy-8α-estra-1,3,5(10)-triene.

40. 1,3-Bis(diethylaminosulfonyloxy)-16β,17β-isopropylidenedioxy-8α-estra-1,3,5(10)-triene.

41. 1,3-Bis(pyrrolidinosulfonyloxy)-16β,17β-isopropylidenedioxy-8α-estra-1,3,5(10)-triene.

42. A pharmaceutical composition comprising a compound according to claim 1 in admixture with a pharmaceutically acceptable carrier.

* * * * *